United States Patent
Sasa et al.

(10) Patent No.: US 10,036,379 B2
(45) Date of Patent: Jul. 31, 2018

(54) PROCESSING LIQUID SUPPLYING APPARATUS, PROCESSING LIQUID SUPPLYING METHOD AND STORAGE MEDIUM

(71) Applicant: TOKYO ELECTRON LIMITED, Tokyo (JP)

(72) Inventors: Takashi Sasa, Koshi (JP); Daiki Shibata, Koshi (JP)

(73) Assignee: Tokyo Electron Limited, Minato-Ku (JP)

( * ) Notice: Subject to any disclaimer, the term of this patent is extended or adjusted under 35 U.S.C. 154(b) by 763 days.

(21) Appl. No.: 14/559,950

(22) Filed: Dec. 4, 2014

(65) Prior Publication Data

US 2015/0159642 A1 Jun. 11, 2015

(30) Foreign Application Priority Data

Dec. 5, 2013 (JP) ................. 2013-252057

(51) Int. Cl.
*F04B 43/12* (2006.01)
*A61M 5/142* (2006.01)
(Continued)

(52) U.S. Cl.
CPC ..... *F04B 43/1238* (2013.01); *A61M 5/14232* (2013.01); *B05C 17/0333* (2013.01);
(Continued)

(58) Field of Classification Search
CPC ................... H01L 21/6715; G03F 7/16; Y10T 137/86027; F04B 43/1261; F04B 43/1238
See application file for complete search history.

(56) References Cited

U.S. PATENT DOCUMENTS

| | | | | |
|---|---|---|---|---|
| 3,101,675 A | * | 8/1963 | Isreeli ................. | F04B 43/12 417/475 |
| 4,019,816 A | * | 4/1977 | Bernhard ............. | G03G 17/04 118/407 |

(Continued)

FOREIGN PATENT DOCUMENTS

| | | |
|---|---|---|
| JP | 2003-118147 A1 | 4/2003 |
| JP | 2008-155155 A1 | 7/2008 |

(Continued)

OTHER PUBLICATIONS

Japanese Office Action (Application No. 2013-252057) dated Mar. 8, 2016.

*Primary Examiner* — Atif Chaudry
(74) *Attorney, Agent, or Firm* — Burr & Brown, PLLC

(57) ABSTRACT

In one embodiment, a feed pump of a tube pump type is used for supplying a processing liquid. The tube pump has a squeezing member that moves from a first axial position of a tube at which the squeezing member starts pinching of the tube, to a second axial position at which the squeezing member leaves the tube after feeding the processing liquid toward an ejecting part such as a nozzle. Only one pinched part pinched between the squeezing member and a guide member is formed between the first axial position and the second axial position of the tube, and the only one pinched part moves along the axial direction of the tube, during feeding of a dose of the processing liquid toward the ejecting part.

14 Claims, 15 Drawing Sheets

(51) Int. Cl.
  *B05C 17/03*  (2006.01)
  *G03F 7/16*  (2006.01)
  *H01L 21/67*  (2006.01)
  *F04B 49/24*  (2006.01)
  *F04B 43/08*  (2006.01)
  *F04B 49/06*  (2006.01)

(52) U.S. Cl.
  CPC .......... *F04B 43/08* (2013.01); *F04B 43/1246* (2013.01); *F04B 43/1253* (2013.01); *F04B 43/1261* (2013.01); *F04B 43/1276* (2013.01); *F04B 43/1284* (2013.01); *F04B 49/06* (2013.01); *F04B 49/065* (2013.01); *F04B 49/24* (2013.01); *G03F 7/16* (2013.01); *H01L 21/6715* (2013.01); *H01L 21/67017* (2013.01); *Y10T 137/794* (2015.04); *Y10T 137/86027* (2015.04)

(56) References Cited

U.S. PATENT DOCUMENTS

| | | | |
|---|---|---|---|
| 6,238,576 B1 * | 5/2001 | Yajima | B01D 35/26 |
| | | | 210/194 |
| 8,728,330 B2 * | 5/2014 | Takeishi | G03F 7/16 |
| | | | 210/167.01 |
| 2012/0181239 A1 | 7/2012 | Furusho et al. | |

FOREIGN PATENT DOCUMENTS

| | | | |
|---|---|---|---|
| JP | 2008-305980 A1 | 12/2008 | |
| JP | 2012-151197 A1 | 8/2012 | |
| WO | WO 2013124728 A1 * | 8/2013 | .......... F04B 43/1261 |

* cited by examiner

PROCESSING LIQUID SUPPLYING APPARATUS, PROCESSING LIQUID SUPPLYING METHOD AND STORAGE MEDIUM

CROSS-REFERENCE TO RELATED APPLICATIONS

This application is based upon and claims the benefit of priority from Japanese patent application No. 2013-252057 filed on Dec. 5, 2013, the entire contents of which are incorporated herein by reference.

FIELD OF THE INVENTION

The present invention relates to a technique for feeding a processing liquid to be supplied to a process object.

BACKGROUND ART

In a photoresist step that is one of semiconductor manufacturing steps, a resist liquid is applied to a surface of a semiconductor wafer (hereinafter referred to as "wafer") as a process object to form a resist film thereon, and the resist film thus obtained is exposed with a predetermined pattern, and is then developed to form a resist pattern.

Some processing liquid supplying apparatus, which ejects a processing liquid, such as a resist liquid or a developing liquid, to a wafer via a nozzle (ejecting part), is configured to supply the processing liquid from a chemical liquid container (processing liquid source) to the nozzle by using a feed pump. For example, JP2008-305980A (see paragraph [0022] and FIG. 2) describes a chemical liquid supplying system, in which a piston is mounted on one end of a bellows body disposed in a container, and a resist liquid is supplied to a coating nozzle by expanding and contracting the bellows body by the piston. In addition, in a chemical liquid supplying system described in JP2012-151197A (see paragraphs [0035] and [0041] and FIGS. 4 and 5), a resist liquid is supplied to an ejecting nozzle by using a diaphragm pump having a diaphragm that reciprocates in a pump chamber.

In a reciprocation pump of like the aforementioned type, a part of the suctioned processing liquid may remain in a dead space in the pump. If the pump does not discharge therefrom all the processing liquid, particles, such as those originated from chips generated during fabrication of the pump and remaining in the pump immediately after installation thereof, stagnate in the pump together with a processing liquid for a long period of time, which delays starting of the wafer processing and/or invites contamination.

A tube pump is known as a pump in which a processing liquid is less likely to stagnate. The tube pump disadvantageously has a large pulsation, so that it is not suitable, in general, for use as a pump that must supply a predetermined amount of a processing liquid stably to each wafer at a suitable timing. JP2003-118147A (see paragraphs 0025 and 0029 and FIGS. 3 to 5) describes that a squeezing roller presses a resilient tube to discharge an ink from a recording head to a waste ink treatment member. However, this document does not describe a technique for stably supplying a processing liquid to a process object.

SUMMARY OF THE INVENTION

The object of the present invention is to provide technique for supplying a processing liquid, by which the amount of the processing liquid stagnated in a processing liquid supplying apparatus can be reduced and the processing liquid can be supplied stably.

In one embodiment of the present invention, there is provided a processing liquid supplying apparatus comprising a feed pump provided in a supply passage, wherein by means of the feed pump, said processing liquid supplying apparatus ejects a processing liquid supplied from a processing liquid source to a process object via an ejecting part, the feed pump including: a resilient tube serving as a part of the supply passage a guide member extending along an axial direction of the tube to support an outer surface of the tube; a squeezing member that moves along the axial direction of the tube with the tube being pinched between the squeezing member and the guide member, thereby to feed the processing liquid; and a moving mechanism that moves the squeezing member from a first axial position of the tube at which the squeezing member starts pinching of the tube, to a second axial position of the tube at which the squeezing member leaves the tube after feeding the processing liquid toward the ejecting part, wherein the squeezing member and the moving mechanism are configured such that only one pinched part pinched between the squeezing member and the guide member is formed between the first axial position and the second axial position of the tube, and said only one pinched part moves along the axial direction of the tube during feeding of a dose of the processing liquid toward the ejecting part.

In another embodiment of the present invention, there is provided a processing liquid supplying method that feeds a processing liquid supplied from a processing liquid source by means of a feed pump provided in a supply passage to eject the processing liquid from an ejecting part to a process object, said method comprising: providing a feed pump having: a resilient tube providing a part of the supply passage; a guide member extending along an axial direction of the tube to support an outer surface of the tube; and a squeezing member that moves along the axial direction of the tube with the tube being pinched between the pushing member and the guide member, thereby to feed the processing liquid; moving the squeezing member to a first axial position of the tube to allow the tube to be pinched between the squeezing member and the guide member; then, moving the squeezing member in the axial direction of the tube toward its downstream side with the tube being pinched between the squeezing member and the guide member, thereby feeding the processing liquid toward the ejecting part; and thereafter, separating the squeezing member from the tube; wherein only one pinched part, which is pinched between the squeezing member and the guide member is formed in the tube between the first axial direction and the second axial direction, and said only one pinched part moves along the axial direction of the tube during feeding of a dose of the processing liquid toward the ejecting part.

According to the foregoing embodiments, since the tube is pinched between the squeezing member and the guide member to feed the processing liquid, there is less possibility that the processing liquid stagnates in the feed pump. In addition, since the tube is squeezed by only the one squeezing member, pulsation caused by the feeding action reduces, whereby a predetermined amount of the processing liquid can be supplied stably.

DETAILED DESCRIPTION OF THE INVENTION

An embodiment of the present invention will be described herebelow with reference to the attached drawings. Explained herein is an example in which a processing liquid supplying apparatus in one embodiment of the present invention is applied to a coating and developing apparatus.

Figure 1:
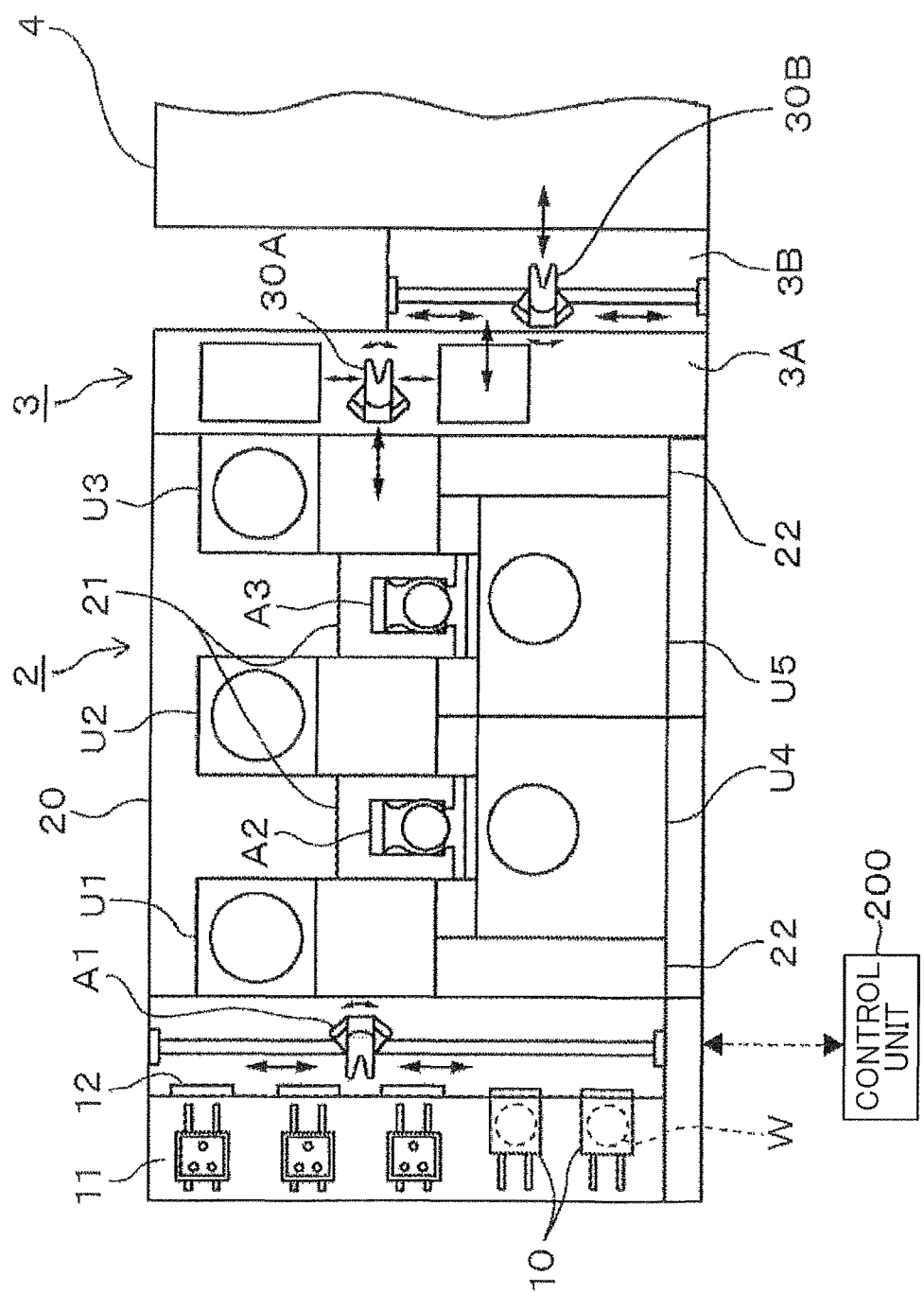
FIG. 1 is a transversely-sectioned plan view of a coating and developing apparatus to which a resist liquid supplying apparatus in one embodiment of the present invention is incorporated therein.
Figure 2:
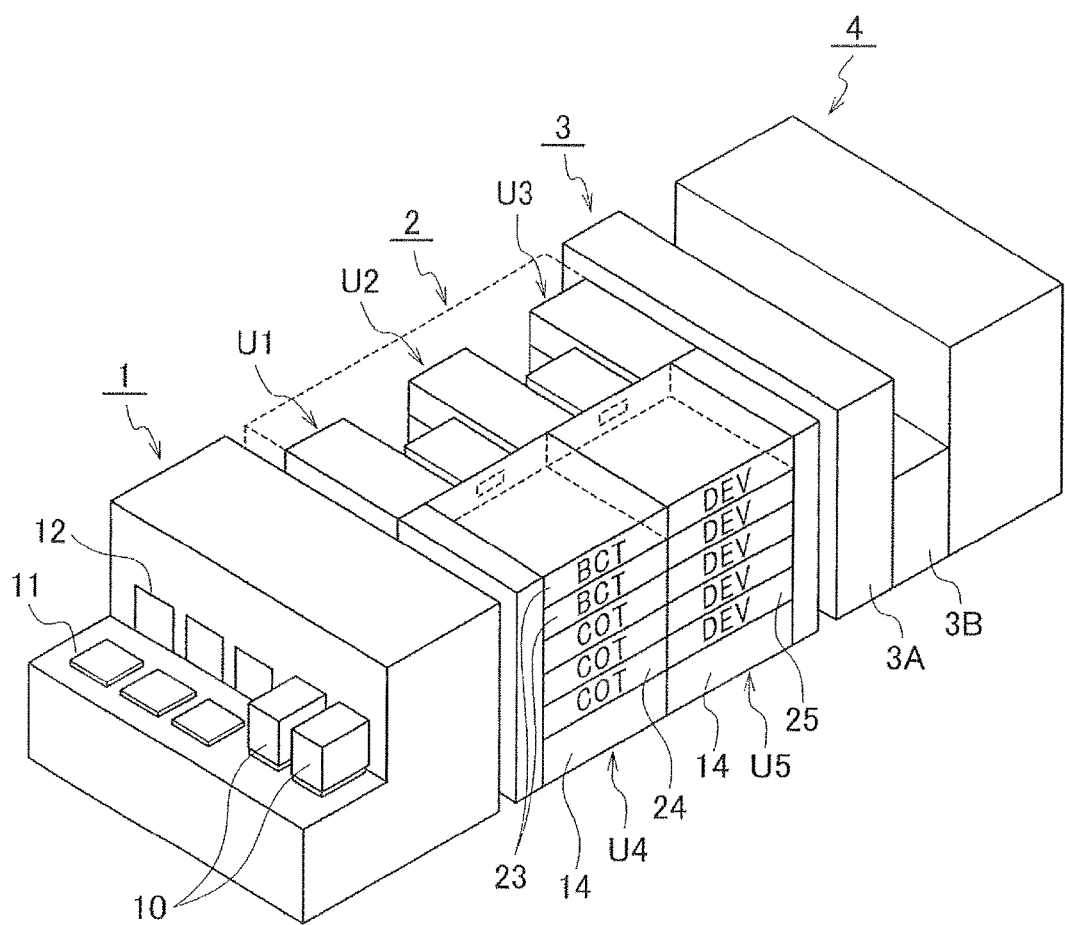
FIG. 2 is a perspective view of the coating and developing apparatus.

As shown in FIGS. 1 and 2, the coating and developing apparatus includes a carrier station 1, a processing section 2, and an interface section 3. The carrier station 1 is used for loading or unloading a carrier 10 which sealingly contains a plurality of, e.g., twenty five wafers W as process objects. The processing section 2 performs a resist coating process (hereinafter referred to as "coating process") and a developing process to the wafers W that are removed from the carrier station 1. The interface section 3 transfers the wafers W between the processing section 2 and an exposure section 4 in which the surface of each wafer W is exposed with a light-transmitting liquid layer being formed on the surface of the wafer W.

The carrier station 1 is provided with: a table 11 on which a plurality of carriers 10 can be placed thereon in a row; an opening and closing part 12 formed in a wall in front of the table 11; and a transfer mechanism A1 that removes a wafer W form the carrier 10 via the opening and closing part 12.

The interface section 3 has a first transfer chamber 3A and a second transfer chamber 3B that are arranged in a back and forth direction between the processing section 2 and the exposure section 4. The first transfer chamber 3A is provided therein with a first wafer transport unit 30A. The second transfer chamber 3B is provided therein with a second wafer transport unit 30B.

The processing section 2 surrounded by a housing 20 is arranged behind and connected to the carrier section 1. The processing section 2 is provided therein with: shelf units U1, U2 and U3 each of which is formed by stacking heating/cooling units; liquid processing units U4 and U5; and main transfer mechanisms A2 and A3 for transferring a wafer W among respective units. The main transfer mechanisms A2 and A3 are disposed in a space surrounded by a partition 21, which comprise a wall on the side of the shelf units U1, U2 and U3, a wall on the side of the liquid processing units U4 and U5, and front and back walls. A temperature/humidity control unit 22 including process liquid temperature control units each for controlling the temperature of the process liquid used in the respective processing units, and temperature/humidity regulating ducts each for controlling the temperature/humidity in the respective processing unit are provided in a space between the carrier station 1 and the processing section 2 and a space between the processing section 2 and the interface section 3.

Each of the shelf units U1, U2 and U3 is formed by stacking, at a plurality of (e.g., ten) levels, various units for performing pre-processes (pre-treatments) and post-processes (post-treatment) of a process (treatment) performed by the liquid processing units U4 and U5. The combination of the units in the shelf units U1, U2 and U3 may include a heating unit (not shown) for heating (backing) a wafer W, a cooling unit (not shown) for cooling a wafer W and so on. Each of the liquid processing units U4 and U5 is configured to supply a processing liquid to a wafer W to perform a liquid treatment to the wafer W. As shown in FIG. 2, each of the liquid processing units U4 and U5 is formed by stacking, at a plurality of (e.g., five) levels, on a chemical liquid containing part 14 for containing a resist and a developer, an antireflection film coating unit (BCT) 23 for applying an antireflection film, a coating unit (COT) 24 for applying a resist liquid to a wafer W, a developing unit (DEV) 25 for developing a wafer W by supplying thereto a developer. The processing liquid supplying apparatus is incorporated into each of the units 23, 24 and 25.

An example of a flow of a wafer W in the foregoing coating and developing apparatus is briefly explained with reference to FIGS. 1 and 2. In the coating and developing apparatus, wafers W belonging to the same production lot are successively transferred. Firstly, when the carrier 10 accommodating, e.g., twenty five, wafers W is placed on the table 11, the opening and closing part 12 opens a lid of the carrier 10. Then, each wafer W is removed from the carrier 10 by the transfer mechanisms A1.

The wafer W thus removed is transferred to the main transfer mechanism A2 via a transition unit (not shown) included in the shelf unit U1. The wafer W is subjected to pre-processes of a coating process, such as an antireflection film forming process performed by the antireflection film coating unit (BCT) 23, and is subjected to a cooling process. Then, the wafer W is coated with a resist liquid by the coating unit (COT) 24. After that, the wafer W is transferred by the main transport means A2 to the heating unit included in the shelves of the shelf units U1 to U3, and the wafer W is heated (baked) there. Thereafter, the wafer W is cooled, and is then loaded into interface section 3 through the transition unit included in the shelf unit U3. After that, the wafer W is cooled, and is then loaded into interface section 3 through the transfer unit of the shelf unit U3.

From the interface section 3, the wafer W is transported to the exposure part 4 by the first wafer transport unit 30A in the first transfer chamber 3A and the second wafer transport unit 30B in the second transport chamber 3B. In the exposure section 4, the wafer W is exposed by an exposure device (not shown) which is disposed to face the surface of the wafer W. After exposed, the wafer W is transferred to the main transfer mechanism A2 along a route reverse to the route along which the wafer W is transported to the exposure section 4, and is transferred to the developing unit (DEV) 25, in which the wafer W is developed so that the resist pattern is formed on the wafer W. Thereafter, the wafer W having the resist pattern is returned to the original carrier 10 placed on the table 11.

Figure 3:
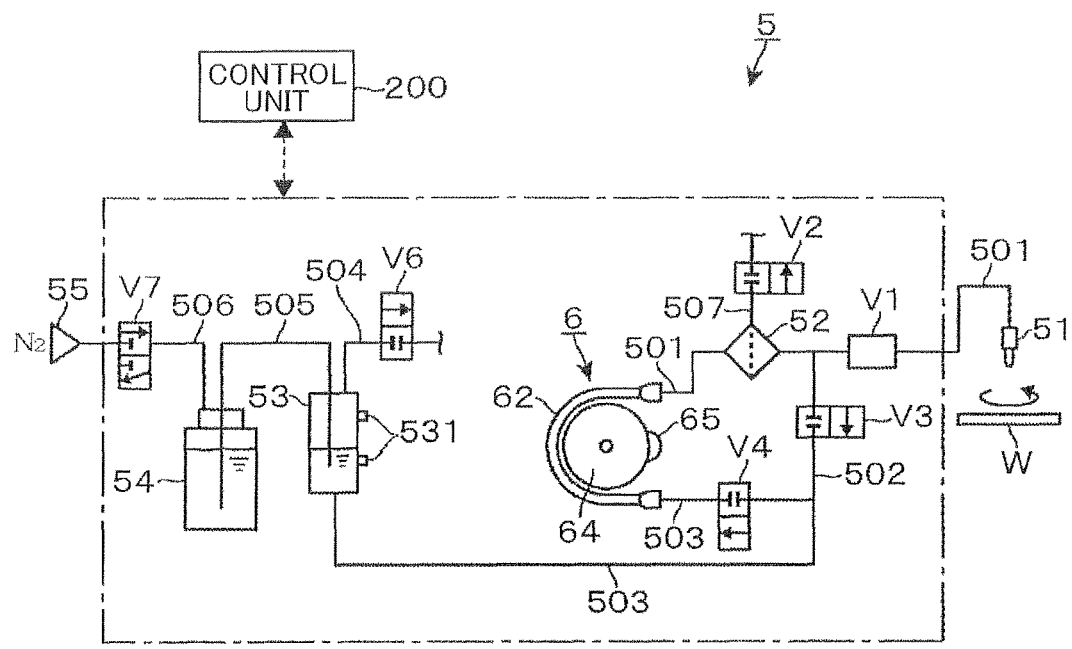
FIG. 3 is a piping diagram of the resist liquid supplying apparatus.

Next, the structure of the processing liquid supplying apparatus incorporated into the units 23, 24 and 25 in the liquid processing units U4 and U5 is described with reference to FIG. 3. FIG. 3 shows a resist liquid supplying apparatus 5 in one embodiment of the processing liquid supplying apparatus that supplies a resist liquid (i.e., processing liquid) to a nozzle 51 of the coating unit (COT) 24. The resist liquid supplying apparatus 5 includes a resist liquid bottle 54, an intermediate tank 53 for temporarily storing a resist liquid transported from the resist liquid bottle 54, and a tube pump 6 (feed pump) for supplying the resist liquid discharged from the intermediate tank 53 to a nozzle 51 (ejecting part).

The resist liquid bottle 54 is a replaceable container that can be installed from outside of the resist liquid supplying apparatus 5. A pressurization line 506 having an electromagnetic switch valve V7 is connected to the resist liquid bottle 54, so that the resist liquid bottle 54 can receive a pressurized inert gas (e.g., nitrogen ($N_2$) gas) from a pressurization gas source 55 to pressurize the resist liquid therein to transport the resist liquid therefrom toward the intermediate tank 53.

The intermediate tank 53 temporarily stores the resist liquid fed from the resist liquid bottle 54 and feeds the resist liquid toward a wafer W. The intermediate tank 53 is equipped with level sensors 531 whose detection result is used for determining the feed start timing and the feed stop timing of the resist liquid from the resist liquid bottle 54. The resist liquid is transported between the resist liquid bottle 54 and the intermediate tank 53 through a transport line 505. A drain line 504 used for discharging the resist liquid in the intermediate tank 53 is connected to an upper part of the intermediate tank 53. The drain line 504 is provided with an electromagnetic shutoff valve V6. The intermediate tank 53 is further provided with a pressurization line (not-shown) for receiving a pressurization gas from the pressurization gas source 55. The resist liquid bottle 54 and the intermediate tank 53 constitute a a processing liquid source in this embodiment.

The intermediate tank 53 is connected to the tube pump 6 through a feed line 503 provided with a shutoff valve V4. The tube pump 6 is connected to the nozzle 51 through a discharge line 501, which is provided with a filter 52 and a dispensing valve V1. A vent line 507 provided with a shutoff valve V2 is disposed on a primary side of the filter 52 (inlet side of a filtering member) to allow the resist liquid containing particles and/or bubbles to be discharged outside from the filter 52. The feed line 503 and the discharge line 501 constitute a supply passage of the resist liquid. The feed line 503 serves as a supply passage on the side of the processing liquid source, and the discharge line 501 serves as a supply passage on the side of the ejecting part (nozzle 51).

A return line 502 (branch passage) branches from the discharge line 501 at a position between the filter 52 and the dispensing valve V1. The return line 502 merges with the feed line 503 at a position upstream of the shutoff valve V4. By using the return line 502, the resist liquid flowing out from the tube pump 6 can be returned again to the tube pump 6. When the return line 502 is used, the dispensing valve V1 and the shutoff valve V3 constitute a switching unit that switches a destination of the resist liquid discharged by the tube pump 6 between the nozzle 51 and the return line 502.

In the resist liquid supplying apparatus 5 in this embodiment, the tube pump 6 has a structure for stably supplying a predetermined amount of the resist liquid to the nozzle 51, while suppressing pulsation. The structure of the tube pump 6 is explained herebelow with reference to FIGS. 4 and 5.

Figure 4:
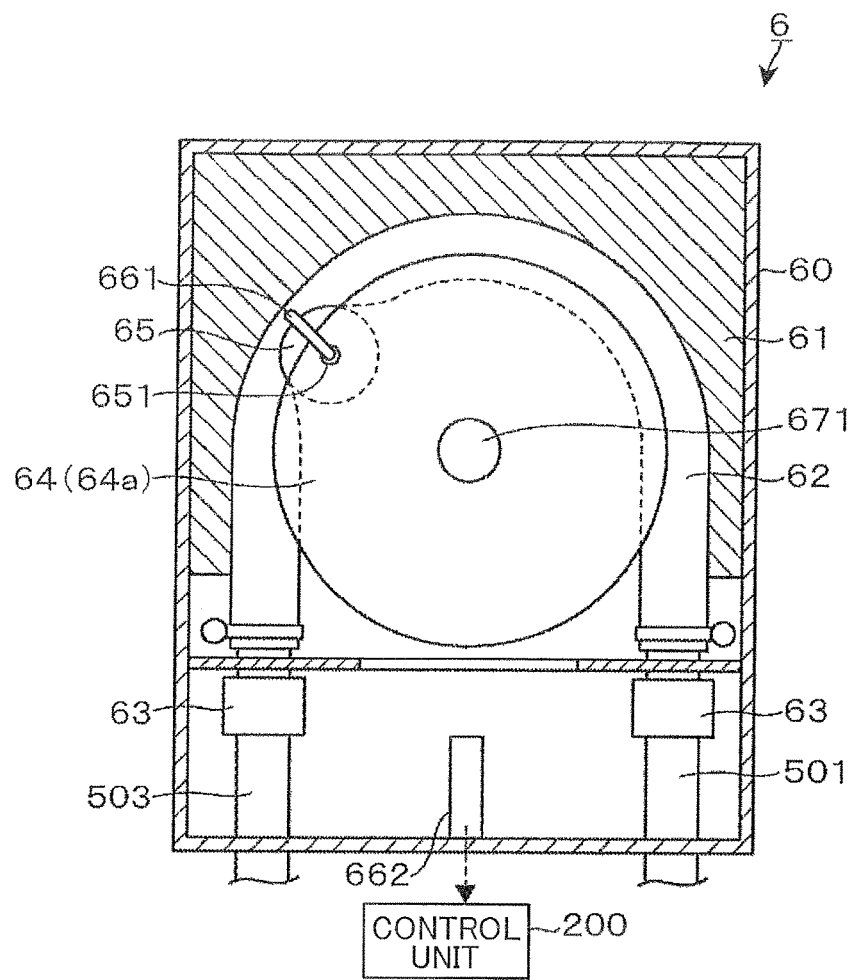
FIG. 4 is a transversely-sectioned plan view of a tube pump provided in the resist liquid supplying apparatus.
Figure 5:
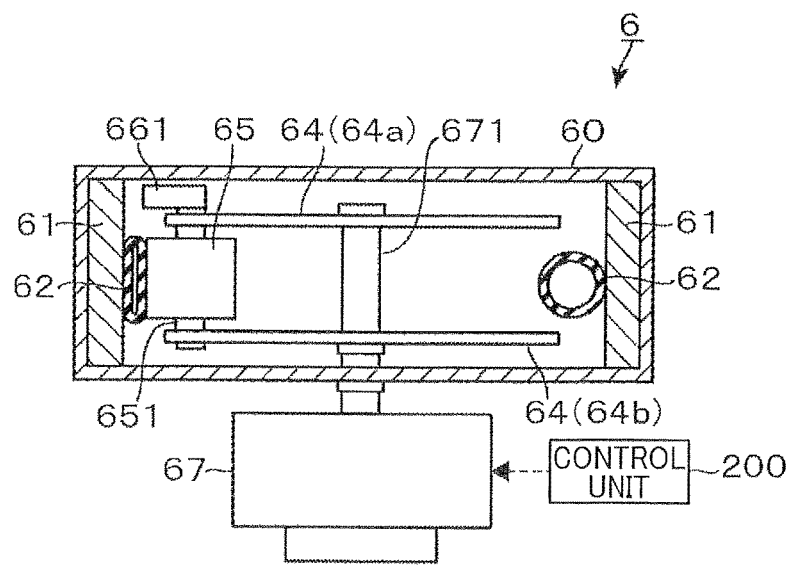
FIG. 5 is a vertically-sectioned side view of the tube pump.

As shown in FIGS. 4 and 5, the tube pump 6 includes: a tube 62 through which the resist liquid flows; a guide member 61 having a wall surface extending along an outer surface of the tube 62 in an axial direction of the tube 62; a rotor 65 (i.e., squeezing member) located opposite to the guide member 61 with respect to the tube 62 so as to pinch the tube 62 between the rotor 65 and the guide member 61; rotating bodies 64 that holds the rotor 65; and an electric motor 67 that drives the rotating body 64 for rotation.

The tube 62 is a resilient pipe made of, e.g., a resin. An inlet end for receiving the resist-liquid and an outlet end for discharging the resist liquid of the tube 62 are respectively connected to the feed line 503 and the discharge line 501 via joints 63. The guide member 61 has a sector-shaped cutout in which the tube 62, the rotor 65 and the rotating body 64 are located. The tube 62 is disposed in a U-shape along an inner side wall having an arcuate shape.

Inside the tube 62 extending along the guide member 61, the two disc-shaped rotating bodies 64 (64a, 64b) are arranged while leaving a vertical gap therebetween. These rotating bodies 64a and 64b are supported by a motor shaft 671. A proximal end of the motor shaft 671 is connected to the electric motor 67 whose rotating direction can be switched. Thus, the rotating bodies 64a and 64b can be rotated in the same direction at the same angle.

A rotor shaft 651 vertically extends through the rotating bodies 64a and 64b, at a position near peripheral portions of the rotating bodies 64a and 64b. The rotor 65 is supported by the rotor shaft 651 to be rotatable about the rotor shaft 651. The rotor 65 is located such that the side peripheral surface of the rotor 65 projects outward beyond the outer periphery of the rotating bodies 64a and 64b. Thus, the rotor 65 can pinch the tube 62 between the side peripheral surface and the guide member 61 so as to compress the tube 62. The tube pump 6 in this embodiment has only one rotor 65.

When the rotating body 64 is rotated with the tube 62 being pinched as described above, the rotor 65 itself is rotated about the rotor shaft 651, and further the rotor 65 is moved to revolve around the motor shaft 671. As a result, the position at which the rotor 65 pinches the tube 62 is moved, so that the resist liquid in the tube 62 is transported in accordance with the movement of the pinched position. The rotating body 64, the motor shaft 671 and the electric motor 67 constitute a moving mechanism of the rotor 65.

The guide member 61, the tube 62, the rotor 65 and the rotating body 64 of the tube pump 6 in this embodiment are disposed in a common housing 60. A photoelectric sensor 662 is disposed in the housing to detect that the rotor 65 is returned to its home position. The photoelectric sensor 662 includes, for example, a light emitting unit and a light receiving unit, which are not shown. When a light beam which is emitted from the light emitting unit and reflected by a reflection plate 661 mounted on an upper end of the rotor 65 and falls on the light receiving unit, the photoelectric sensor 662 detects that the rotor 65 is located at its home position. In the tube pump 6 in this embodiment, the home position is set at a position within a region in which the roller 65 is remote from the tube 62 and thus does not pinch the tube 62.

As shown in FIG. 1, the coating and developing apparatus is equipped with a control unit 200 that controls all the operations of the coating and developing apparatus. As shown in FIG. 3, the control unit 200 also controls the resist liquid supplying apparatus 5. The control unit 200 comprises a computer including a CPU and a storage unit. The storage unit stores a program for controlling the resist liquid supplying apparatus 5. Namely, based on the program, the resist liquid is fed from the resist liquid bottle 54 to the intermediate tank 53, and the resist liquid in the intermediate tank 53 is supplied to the nozzle 51 by the tube pump 6. The program is stored in a storage medium such as a hard disc, a compact disc, a magnet-optical disc or a memory card, and is installed from there to the computer.

As shown in FIGS. 4 and 5, in connection with the controlling of the operation of the tube pump 6, the control unit 200 receives a signal informing that reflected light of the reflection plate 661 is detected by the photoelectric sensor 662, so as to recognize that the rotor 65 is located at its home position. In addition, the control unit 200 outputs to the electric motor 67 a signal for instructing the rotating direction and the rotating amount (rotating angle) of the rotating body 64. Thus, the control unit 200 can recognize the current position of the rotor 65 based on the rotating direction and the rotating amount of the rotating body 64 from its home position.

The operation of the resist liquid supplying apparatus 5 having the foregoing structure is then explained with reference to FIGS. 6 to 10. For simplicity of the drawings, the guide member 61, the photoelectric sensor 662 and so on are not shown in FIGS. 6 to 13.

The shutoff valve V4 on the feed line 503 and the dispensing valve V1 on the discharge line 501 are firstly opened so that an opened flow path extending from the resist liquid bottle 54 to the nozzle 51 is established. Then, the switching valve V7 of the pressurization line 506 is opened to receive the pressurization gas from the pressurization gas source 55. When the interior of the resist liquid bottle 54 is pressurized by the pressurization gas, the resist liquid in the resist liquid bolt 54 is fed to the intermediate tank 53.

Figure 6:
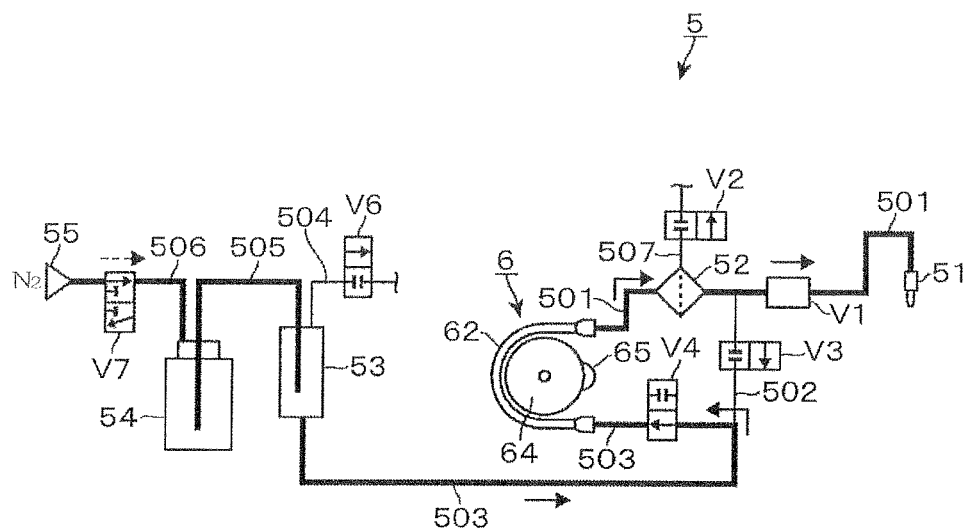
FIG. 6 is a first explanatory diagram for explaining an operation of the resist liquid supplying apparatus.

When the interior of the intermediate tank 53 is pressurized by the pressurization gas received from the not-shown pressurization line, the flow path extending from the feed line 503 to the nozzle 51 via the tube pump 6 and the filter 52 is filled with the resist liquid and thus the air is vented from the flow path (FIG. 6). Then, the dispensing valve V1 is closed and the shutoff valve V3 is opened, so that the route of the flow path is switched such that it does not extend to the nozzle 51 but extends into the return line 502. Further, the shutoff valve V2 on the vent line 507 is opened and the pressurization of the intermediate tank 53 is continued, so that the pipe of the return line 502 is filled with the resist liquid, and air is discharged to the vent line 507 (This operation is not shown.). During these operations, the rotor 65 is located at its home position, so that the resist-liquid filling operation is performed with the tube 62 not being pinched.

Figure 7:
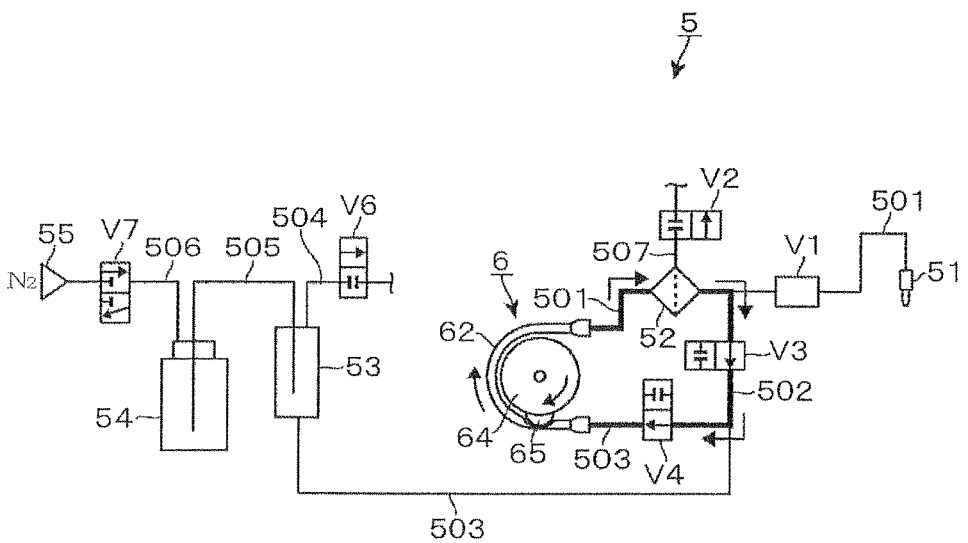
FIG. 7 is a second explanatory diagram for explaining the operation of the resist liquid supplying apparatus.

After the flow path comprising lines 503, 62, 501 and 502 in the resist liquid supplying apparatus 5 have been vented, the supply of the pressurization gas is stopped, and the shutoff valve V2 on the vent line 507 of the filter 52 is closed, while the outlet of the tube pump 6 is continuously connected to the return line 502. After that, the rotating body 64 is rotated, so that the rotor 65 standing-by at its home position is moved to a first axial position of the tube 62 at which pinching of the tube 62 between the rotor 65 and the guide member 61 starts (FIG. 7).

When the rotor 65 is moved to the first axial position of the tube 62, the tube 62 is pinched or squeezed. When the rotor 65 is further moved, the resist liquid is transported in the tube 62 so as to be pushed out (squeezed) from the tube pump 6. At this time, as shown in FIG. 7, since the discharge line 501 is connected to the return line 502, and a part of the discharge line 501 on the side of the nozzle 51 is closed, the resist liquid pushed out from the tube 62 by the rotor 65 is returned again to the inlet side of the tube pump 6.

The filter 52 is provided on the outlet side of the tube pump 6, whereby the resist liquid, which is once filtered by the filter 52, is returned to the tube pump 6. Thus, when the resist liquid is discharged from the tube pump 6 toward a wafer W (see FIG. 8 described herebelow), the returned resist liquid can be filtered again by the filter 52. As a result, the resist liquid having less particles and/or bubbles can be ejected to the wafer W.

When the rotor 65 is further moved to reach a predetermined ejection-start position (e.g., the position shown in FIG. 7), the movement of the rotor 65 is stopped. When the position of the rotor 65 is adjusted in the aforementioned manner, the resist liquid pushed out from the tube pump 6 flows toward the return line 502 so that unnecessary ejection of the resist liquid from the nozzle 51 is prevented. In addition, since the return line 502 is connected to the outlet side of the tube pump 6 so as to return the resist liquid having been pushed out from the tube pump 6 back to the tube pump 6, the resist liquid can be used without waste.

Figure 8:
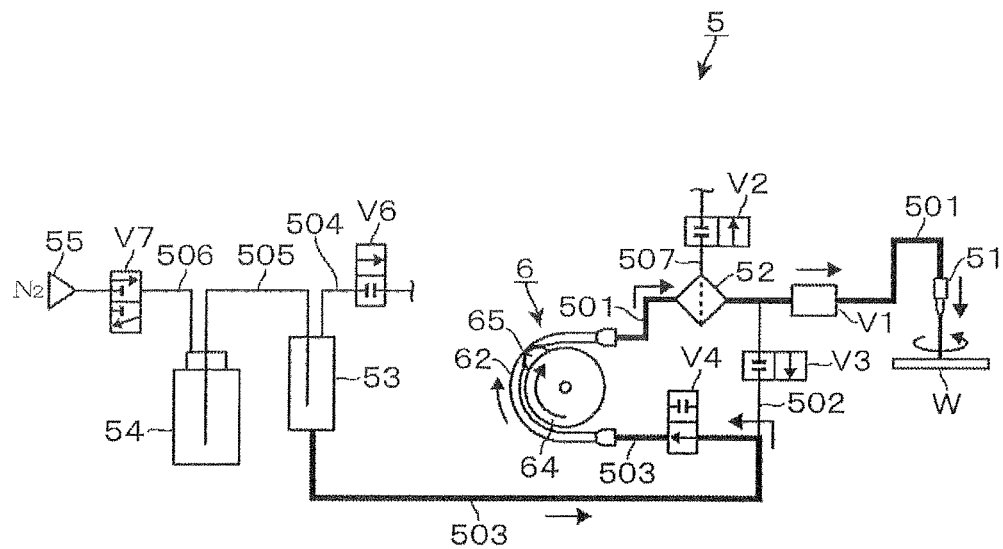
FIG. 8 is a third explanatory diagram for explaining the operation of the resist liquid supplying apparatus.

When the movement of the rotor 65 is stopped at its ejection-start position and the pressure of the resist liquid in the tube 62 and the discharge line 501 becomes stable, as shown in FIG. 8, the shutoff valve V3 on the return line 502 is closed and the dispensing valve V1 on the discharge line 501 is opened, so that the destination of the resist liquid discharged from the tube pump 6 is switched to the nozzle 51. Thereafter, the rotor 65 is moved toward the outlet of the tube 62 connected to the discharge line 501, the resist liquid pushed out from the tube pump 6 is filtered by the filter 52, and is then supplied to the nozzle 51. The resist liquid supplied to the nozzle 51 is ejected onto the surface of the wafer W, which is rotated about a vertical axis, to expand over the surface of the wafer W thereby to form a resist film.

In this manner, by moving the rotor 65 from the predetermined ejection-start position to an ejection-finish position so as to transport the resist liquid in the tube 62, a predetermined amount of the resist liquid can be accurately supplied each time toward the nozzle 51. At this time, the resist liquid is fed in such a manner not only that the distance from the ejection-start position to the ejection-finish position is made constant, but also that the ejection-start position is fixed. Due to such an operation, as compared with a case in which the ejection-start position changes for each time, the amount of the resist liquid to be supplied to the nozzle 51 can be made more stable. This advantageous effect was confirmed by an experiment (see Experiment 2 described below).

Furthermore, since the only one rotor 65 squeezes the tube 62, the resist liquid can be stably supplied with less pressure variation (see Experiment 1 described below), as compared with the case where the processing liquid is transported by using a tube pump 6c including the plurality of rotors 65 (FIG. 18) which simultaneously pinch the tube 62 at a plurality of positions (see Comparative Example described later). As a result, the resist liquid can be ejected from the nozzle 51 without intermittence, whereby an excellent resist film can be formed.

After the rotor 65 has been moved to the ejection-finish position of the resist liquid, an operation for removing bubbles trapped by the filter 52 may be performed according to need, (e.g., every predetermined number of processes of wafers W or every predetermined period of time (FIG. 9)). When the bubble removal operation is performed, the dispensing valve V1 on the discharge line 501 is closed, and the shutoff valve V2 on the vent line 507 is opened. Then, the rotor 65 is further moved from the ejection-finish position toward the outlet of the tube 62 connected to the discharge line 501 to supply the resist liquid toward the filter 52, so as to push out the bubble-containing resist liquid that stagnates in the filter 52.

Figure 9:
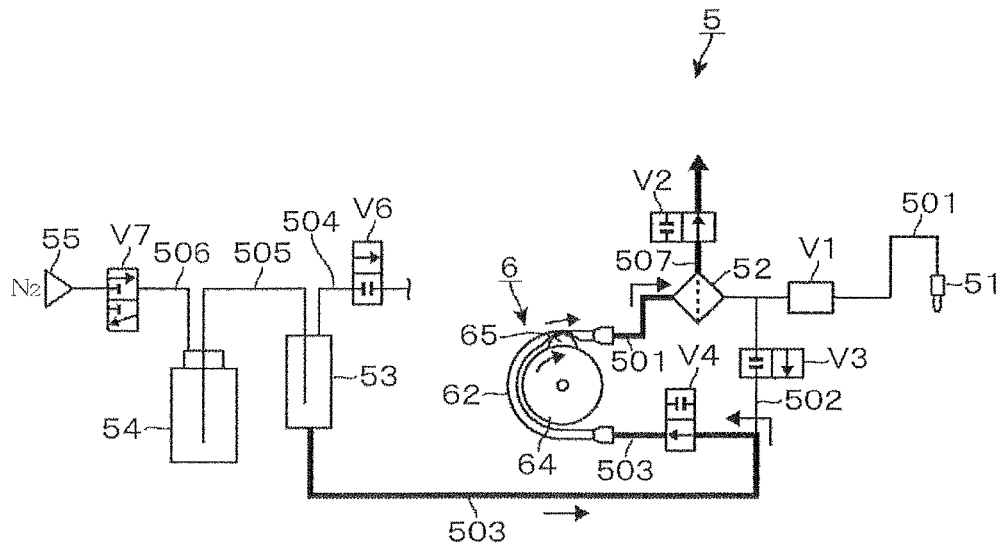
FIG. 9 is a fourth explanatory diagram for explaining the operation of the resist liquid supplying apparatus.

In the operation shown in FIG. 9, the rotor 65 is moved to the ejection-finish position of the resist liquid (second axial position of the tube), and thereafter the bubble removal operation follows thereto. However, the bubble removal operation may be performed in the following manner. Namely, the rotor 65 is moved from the ejection-finish position to the home position, with the outlet port of the filter 52 being communicated with the return line 502. Then, the rotor 65 is again moved forward from the home position to a position at which the rotor 65 pinches the tube 62. After that, the valves V1 to V4 are switched to the conditions as shown in FIG. 9, and the bubble removal operation is performed.

Figure 10:
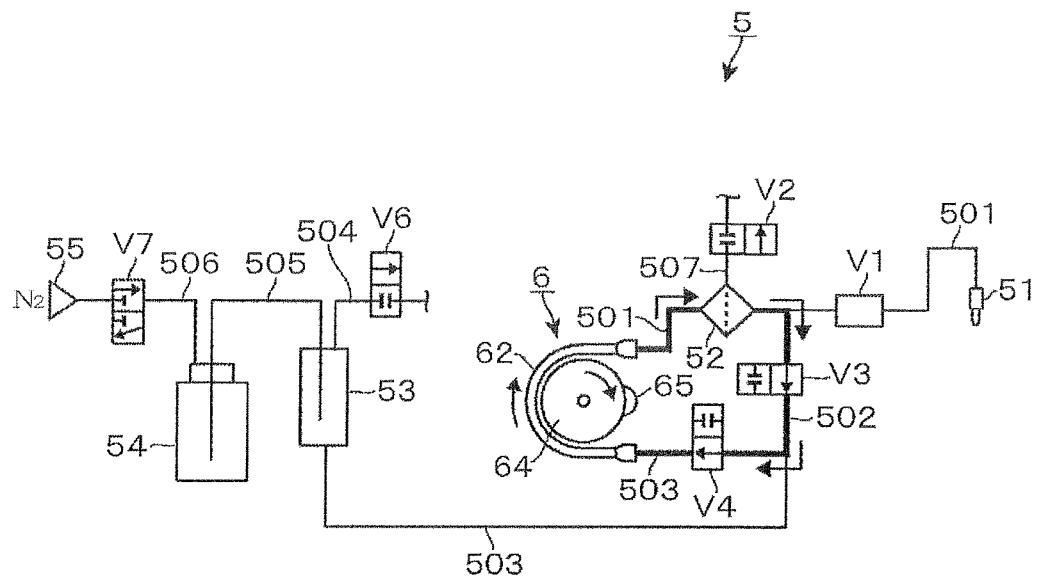
FIG. 10 is a fifth explanatory diagram for explaining the operation of the resist liquid supplying apparatus.

The aforementioned operations may be summarized as follows. When the bubble removal operation is not performed, starting from the state (see valves V1 to V4) as shown in FIG. 8, the dispensing valve V1 on the discharge line 501 is closed, and the shutoff valve V3 on the return line 502 is opened. When the bubble removal operation is performed, starting from the state (see valves V1 to V4) as shown in FIG. 9, the shutoff valve V2 on the vent line 507 is closed. Thereafter, the rotor 65, which is stopped at the ejection-finish position or the finish position of the bubble removal operation, is further moved toward the outlet of the tube 62, so that the rotor 65 leaves the tube 62 to return to the home position (FIG. 10).

Also in the aforementioned operation, the resist liquid pushed out from the tube pump 6 flows into the return line 502, so that unnecessary ejection of the resist liquid from the nozzle 51 is prevented. In addition, since the resist liquid pushed out from the tube pump 6 is returned to the tube pump 6, the resist liquid can be uses without waste. By repeating the aforementioned operations shown in FIG. 7, FIG. 8, (FIG. 9 according to need) and FIG. 10 sequentially, a predetermined amount of the resist liquid can be stably supplied to each of plural wafers W and thus an excellent resist-film coating process can be performed to each of plural wafers W.

The resist liquid supplying apparatus 5 in this embodiment is advantageous in the following respects. Since the tube 62 is pressed by the rotor 65 to feed the resist liquid, the resist liquid is not likely to stagnate in the tube pump 6. In addition, since only one rotor 65 is used for pinching and squeezing the tube 62 to feed a dose of resist liquid (i.e., the amount of the resist liquid to be ejected to one wafer), pulsation (pressure fluctuation) caused by the liquid feeding action decreases, whereby a predetermined amount of the resist liquid can be stably supplied each time.

Next, degassing of the resist liquid using the resist liquid supplying apparatus 5 is explained with reference to FIGS. 11 and 12, in which constituent elements identical to those shown in FIGS. 3 to 10 are designated by the same reference numbers as those of FIGS. 3 to 10. In starting of the degassing operation, the shutoff valve V4 is opened and the flow path downstream of the shutoff valve V4 (i.e., the feed line 503 to the tube 62) is filled with the resist liquid. At this time, the dispensing valve V1 on the discharge line 501 and the shutoff valve V2 on the vent line 507 are closed, and the shutoff valve V3 on the return line 502 is opened. Then, the rotor 65 is moved from the home position to a position where the rotor 65 is brought into contact with the tube 62 with the tube 62 being pinched between the rotor 65 and the guide member 61. Thereafter, the shutoff valve V4 on the feed line 503 is closed (FIG. 11).

After the shutoff valve V4 has been closed, even when the rotor 65 is moved toward the outlet of the tube 62, the resist liquid is not supplied into the tube 62 from the upstream side of the tube 62. Thus, as shown FIG. 11, the tube 62 remains collapsed. However, since the resilient tube 62 has a restoring force to return to its original shape, the interior of a part of the feed line 503 extending from the shutoff valve V4 to the inlet of the tube 62 is depressurized, so that a gas dissolved in the resist liquid is degassed. At this time, the destination of the resist liquid from the tube pump 6 may be the vent line 507, instead of the return line 502. In a preparatory experiment employing a resin tube (62) having an internal diameter of 6 mm and a thickness of 1.25 mm, it was confirmed that a negative pressure of −70 kPa relative to the atmospheric pressure could be achieved the restoring force of the tube 62. This value of the negative pressure is sufficient for the resist liquid to be degassed.

Figure 11:
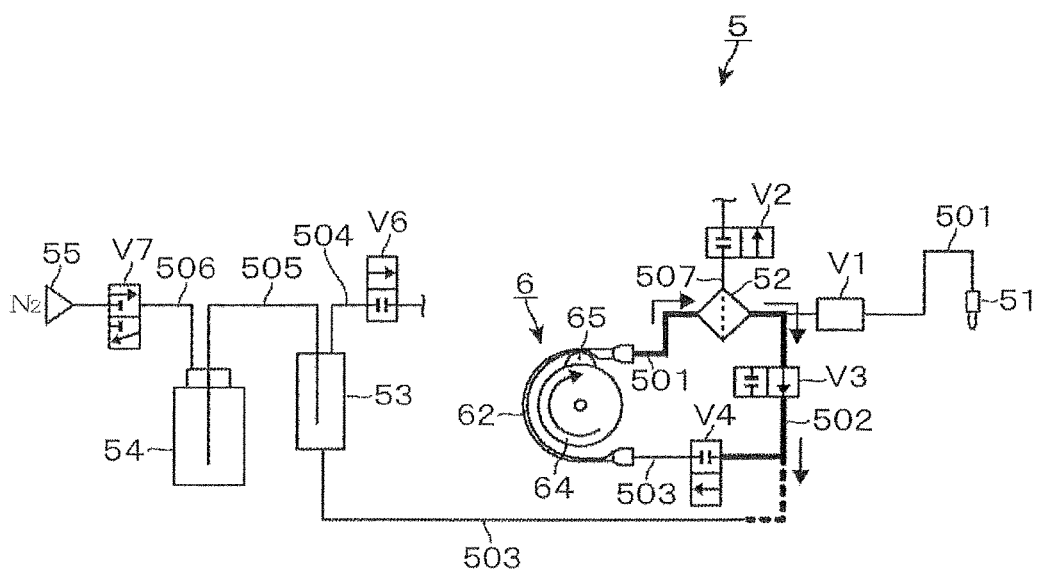
FIG. 11 is a first explanatory diagram for explaining another operation of the resist liquid supplying apparatus.
Figure 12:
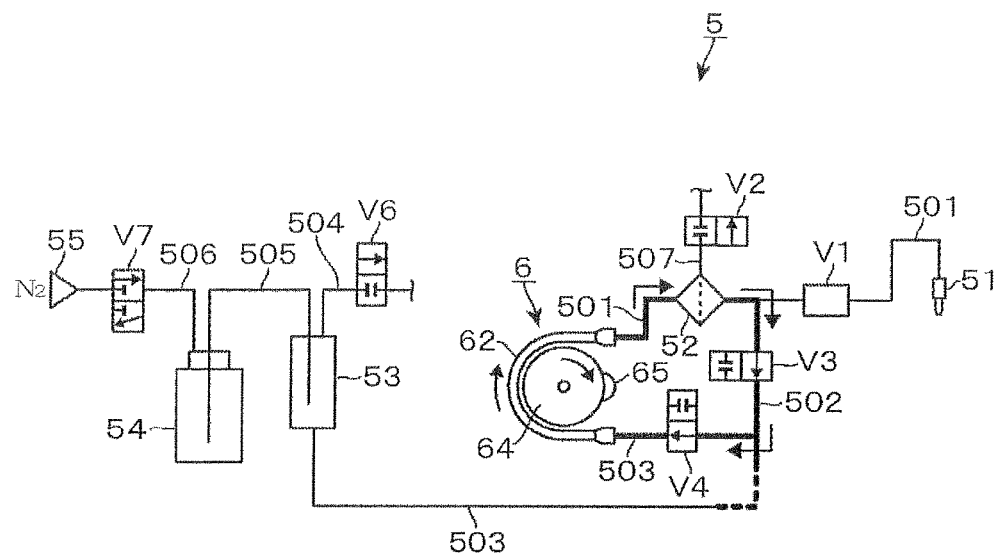
FIG. 12 is a second explanatory diagram for explaining said another operation of the resist liquid supplying apparatus.

After the state shown in FIG. 11 has been maintained for a predetermined period of time thereby to complete the degassing operation, the shutoff valve V4 on the feed line 503 is opened, and the rotor 65 is moved (forward) in the same rotating direction up to the home position. As a result, the tube 62 returns to the original shape by its resilience, so that the degassed resist liquid comes into the tube 62. Following thereto, the rotor 65 is moved so that the tube 62 is pinched between the rotor and the guide member 61 and the rotor 65 is further moved forward so as to feed the processing liquid. Thus, the degassed resist liquid passes through the filter 52, and bubbles generated in the resist liquid upon degassing are removed by the filter (FIG. 12). Thereafter, the bubble removal operation is performed at a suitable timing, the bubbles removed by the filter 52 are discharged outside from the filter as shown in FIG. 9.

Figure 13:
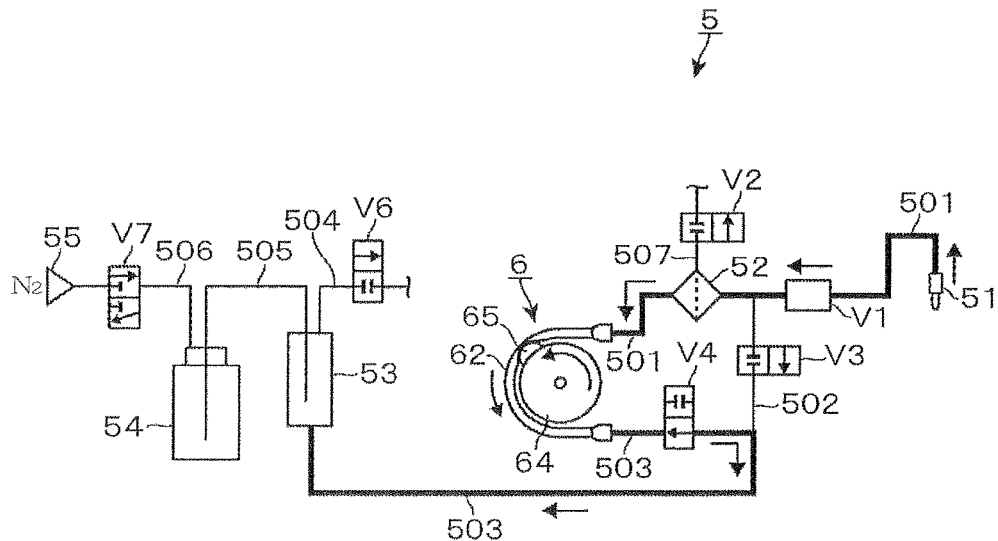
FIG. 13 is an explanatory diagram for explaining yet another operation of the resist liquid supplying apparatus.

Further, the resist liquid supplying apparatus 5 can be used for an operation for collecting the resist liquid from the discharge line 501, when the operation of the coating and developing apparatus is stopped or when the resist liquid supplying apparatus 5 is under maintenance. In this case, the rotor 65 is driven for reverse rotation (the rotating direction is opposite to the rotation direction for feeding of the resist liquid to the nozzle 51) to bring the rotor 65 into contact with the tube 62 from the outlet side of the tube 62 (FIG. 13). After that, the dispensing valve V1 on the discharge line 501 and the shutoff valve V4 on the feed line 503 are opened with the shutoff valve V3 on the return line 502 and the shutoff valve V2 on the vent line 507 being closed, so that an opened flow path (shown by bold lines in FIG. 13) extends from the nozzle 51 to the intermediate tank 53. Under the situation, the rotor 65 is reversely moved toward the inlet of the tube. Owing to this action, the resist liquid remaining in the discharge line 501 is suctioned into the tube 62; and the resist liquid remaining in the tube 62 is returned toward the feed line 503 (and toward the intermediate tank 53).

Next, variations of the tube pump 6 will be described. In the tube pump 6 shown in FIGS. 4 and 5, the guide member 61 may be replaced with another guide member 61 selected from the plurality of guide members 61 having different lengths (i.e., the length of the inner peripheral wall of each guide member 61 opposing to the rotor 65) measured in the axial direction of the tube 62. Thus, the distance between the ejection-start position and the ejection-finish position can be changed, whereby the amount of the resist liquid to be supplied to the nozzle 51 can be changed. Alternatively, the tube 62 may be replaced with another tube 62 that is selected from the plurality of tubes 62 having different inner diameters, whereby the amount of the resist liquid to be supplied to the nozzle 51 can be changed.

Figure 14:
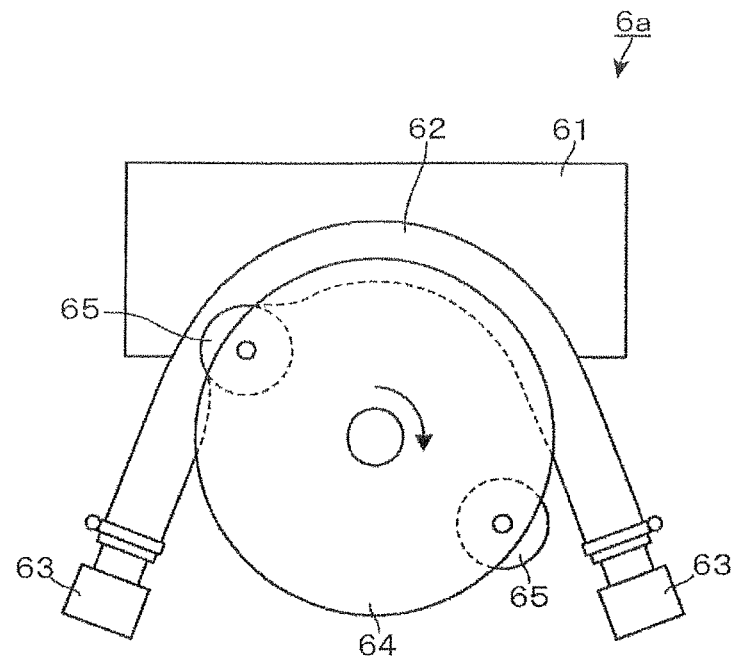
FIG. 14 is a transversely-sectioned plan view of a tube pump in one modification.

In addition, the rotating body 64 may have a plurality of rotors 65, as illustrated in FIG. 14 showing a tube pump 6a. In this case, the angular interval of the rotors 65 and/or and the length of the guide member 61 measured in the axial direction of the tube 62 are suitably adjusted, such that, when one of the rotors 65 pinching the tube 62 to feed the resist liquid, the other rotor or rotors 65 do not pinch the tube 62. Thus, since the liquid feeding action is always performed by only one rotor 65, occurrence of pulsation can be restrained whereby a predetermined amount of the resist liquid can be stably supplied each time.

Figure 15:
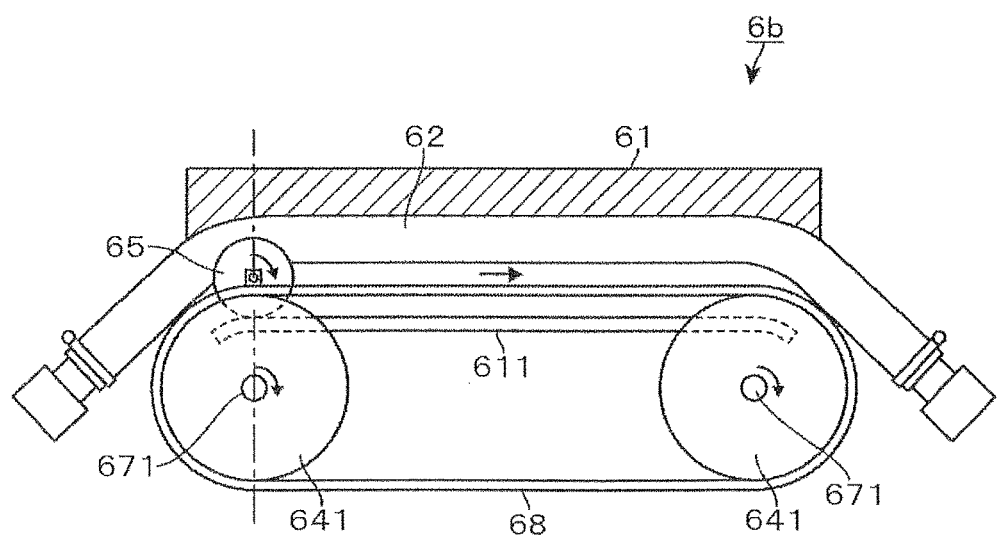
FIG. 15 is a transversely-sectioned plan view of a tube pump in another variation.
Figure 16:
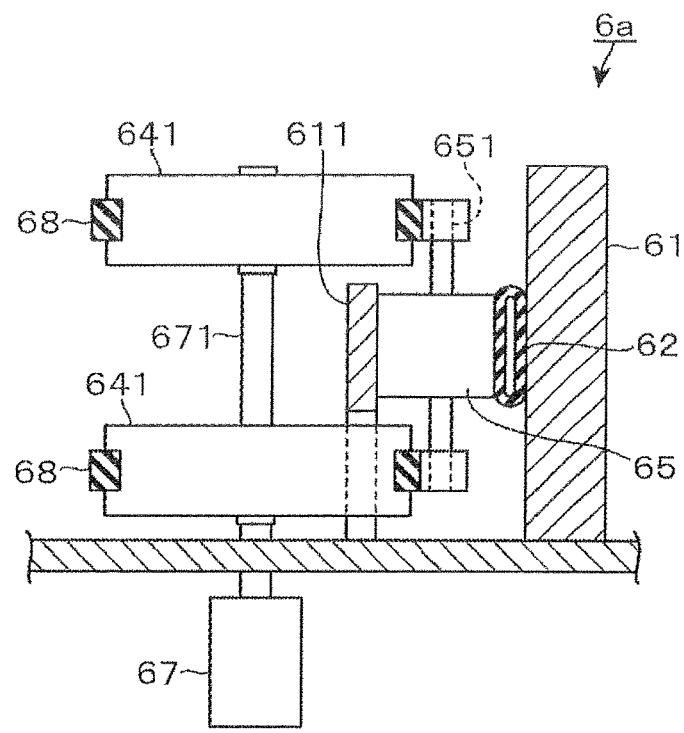
FIG. 16 is a vertically-sectioned side view of the tube pump of FIG. 15.

Furthermore, the configurations of the tube 62 and the rotor 65 moving mechanism are not limited to those of the tube pumps 6 and 6a shown in FIGS. 4 and 14. FIGS. 15 and 16 show another type of tube pump 6b, in which the guide member 61 is disposed along a linearly extending tube 62 (instead of the tube 62 that is curved in a U-shape), and the rotor 65 is guided by a guide wall 611, which is separated from the guide member 61. The tube pump 6b has two driving belts 63 wound around pulleys 641 arranged with a vertical gap therebetween, and a rotor shaft 651 connecting the driving belts 68 to each other.

The one pulley 641 with the driving belt 68 and the other pulley 641 with the driving belt 68 are supported by the common rotor shaft 651. When the driving belts 68 are rotated by an electric motor 67 disposed on a proximal end of the rotor shaft 651, the rotor 65 is moved so that the resist liquid is supplied. In the tube pump 6b in this example, the guide wall 611 in addition to the guide member 61 constitutes the guide member. The pulleys 641, the rotor shafts 651, the electric motor 67 and the driving belts 68 constitute the moving mechanism.

Figure 17:
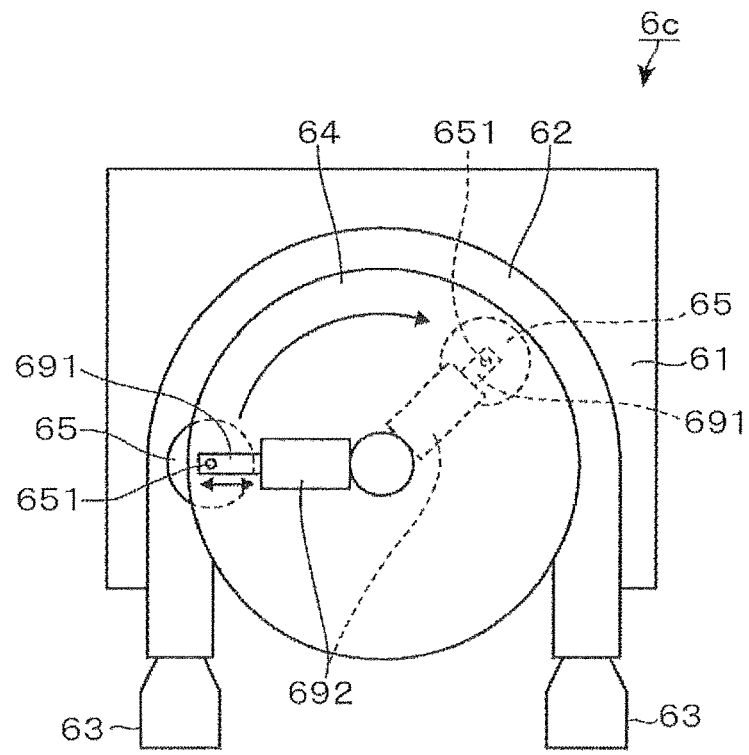
FIG. 17 is a transversely-sectioned plan view of a tube pump in yet another modification.

It is not necessary for the resist liquid supplying apparatus 5 to have the return line 502. For example, as illustrated in FIG. 17 showing a tube pump 6c, the rotor shaft 651 may be held by a shaft 691 which is retractable in the radial direction of the rotating body 64 by a driving unit 692. In this embodiment, until the rotor 65 reaches the ejection-start position (angular position), the rotor 65 is retracted to a radial position at which the rotor 65 does not contact with the tube 62. After the rotor 65 has reached the ejection-start position (angular position), the rotor 65 is moved to a radial position at which the side peripheral surface of the rotor 65 projects from the rotating body 64 so as to pinch the tube 62.

After feeding the resist liquid, the rotor 65 is retracted to a radial position at which the rotor 65 dose not contact with the tube 62, and the rotor 65 is moved to the home position (angular position) with the rotor 65 being retracted. In the embodiment shown FIG. 17, the rotor 65 is not in contact with the tube 62 while the rotor 65 is moved in a region other than the region between the ejection-start position and the ejection-finish position. Thus, unnecessarily ejection of the resist liquid from the nozzle 51 can be prevented, even if the resist liquid is not introduced into the return line 502. In addition, since the rotor 65 can be moved without pressing the tube 62 in this embodiment, the rotor 65 may be moved to the ejection-start position either from upstream side or downstream side of the tube 62.

Moreover, the structure of the resist liquid supplying apparatus 5 may be modified such that the return line 502 is branched from the discharge line 501 at a position upstream of the filter 52. In this case, is preferable that another filter is provided on the return line 502.

In addition, the operation for returning the rotor 65 to the home position may not be necessarily performed every time. For example, a plurality of ejection-start positions (ejection-stop positions) may be set on the tube 62 at regular intervals along the axial direction of the tube 62; in this case, when the rotor 65 reaches a first ejection-finish position after feeding a dose of the resist liquid, the supply of the resist liquid is stopped and the wafer is replaced with another wafer W, and then the resist liquid is supplied to the next wafer W by moving the rotor 65 from the first ejection-finish position as a second ejection start position. As described later (Experiment 2), as long as the resist liquid of substantially the same amount can be supplied each time even if the ejection-start positions are different from each other, the aforementioned operation can be performed (see (Examples 2-1 and 2-2)).

The description has been made for a case where resist liquid supplying apparatus 5 in one embodiment of the processing liquid supplying apparatus is provided in the resist coating unit installed in the coating and developing apparatus. However, not limited to the foregoing embodiment, the processing liquid supplying apparatus may be incorporate into various types of liquid processing units to supply various types of processing liquids to substrates. For example, the processing liquid supplying apparatus may be incorporated into the aforementioned antireflection film coating unit (BCT) 23 to supply a material liquid of an antireflection film, or into the developing unit (DEV) 25 to supply a developing liquid, or into a protection film forming unit (ITC) to supply a material liquid of a protective film to be formed on the resist film.

Furthermore, not limited to the liquid processing units of the coating and developing apparatus, the processing liquid supplying apparatus may be incorporated into a liquid processing unit to supply an acid or alkaline cleaning liquid for cleaning a wafer W. A process object to be supplied with the processing liquid through the processing liquid supplying apparatus is not limited to a semiconductor wafer but may be a various types of substrates such as a glass substrate for an FPD (Flat Panel Display).

EXAMPLES (Experiment 1)

Figure 18:
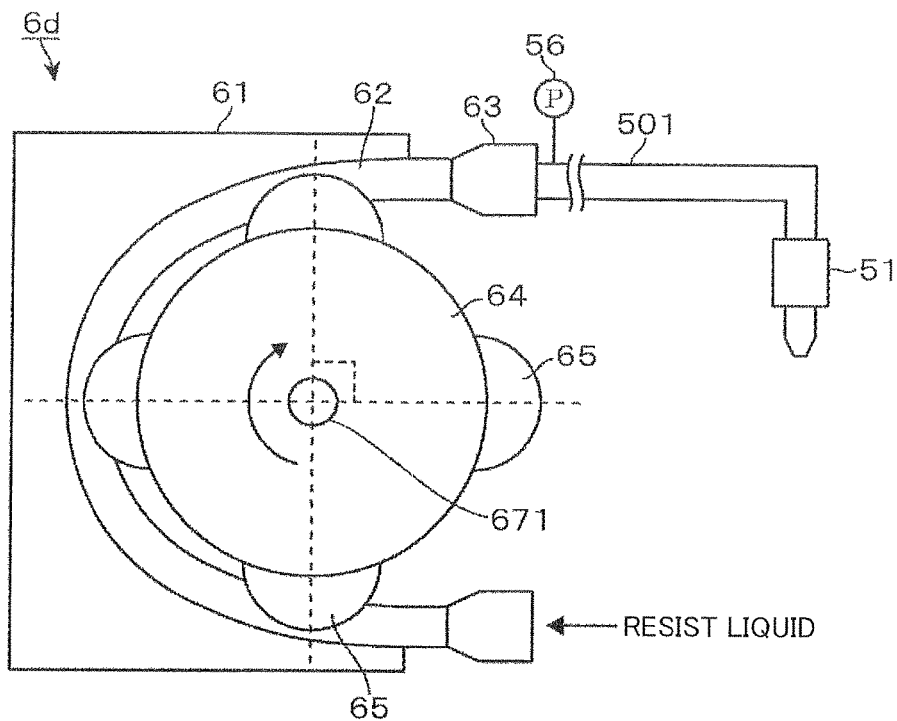
FIG. 18 is a plan view showing the structure of a tube pump used in Comparative Example 1.

An experiment was conducted in which a resist liquid was supplied to the nozzle 51 using the tube pump 6 having only one rotor 65 as shown in FIGS. 4 and 5, and using the tube pump 6d having four rotors 65 as shown in FIG. 18. The change of feed pressure of the resist liquid with time and the ejecting condition of the resist liquid from the nozzle 51 were observed.

A. Experiment Condition

Example 1

The tube pump 6 shown in FIGS. 4 and 5 was installed into the resist liquid supplying apparatus 5 shown in FIG. 3. The rotor 65 was moved such that the flow rate of the resist liquid discharged from the tube pump 6 was 0.5 ml/second. The change of the feed pressure of the resist liquid with time was measured by a manometer (pressure gauge) 56 disposed on the discharge line 501 on the outlet side of the tube pump 6. In addition, the ejecting (discharging) state of the resist liquid from the nozzle 51 was visually observed. The tube 62 employed in the experiment is a resin tube having an internal diameter of 6 mm and a thickness of 1.25 mm.

Comparative Example 1

The change of a feed pressure of the resist liquid with time was measured and the ejecting state of the resist liquid from the nozzle 51 was visually observed under the same conditions as those of Experiment 1. Comparative Example 1 employed a tube pump having four rotors 65 arranged on the outer periphery of the rotating body 64 at regular angular intervals, as shown in FIG. 18. In Comparative Example 1, the tube 62 was simultaneously squeezed by the two or three rotors 65 when the tube pump 6d discharged a dose of resist liquid.

B. Experiment Result

Figure 19:
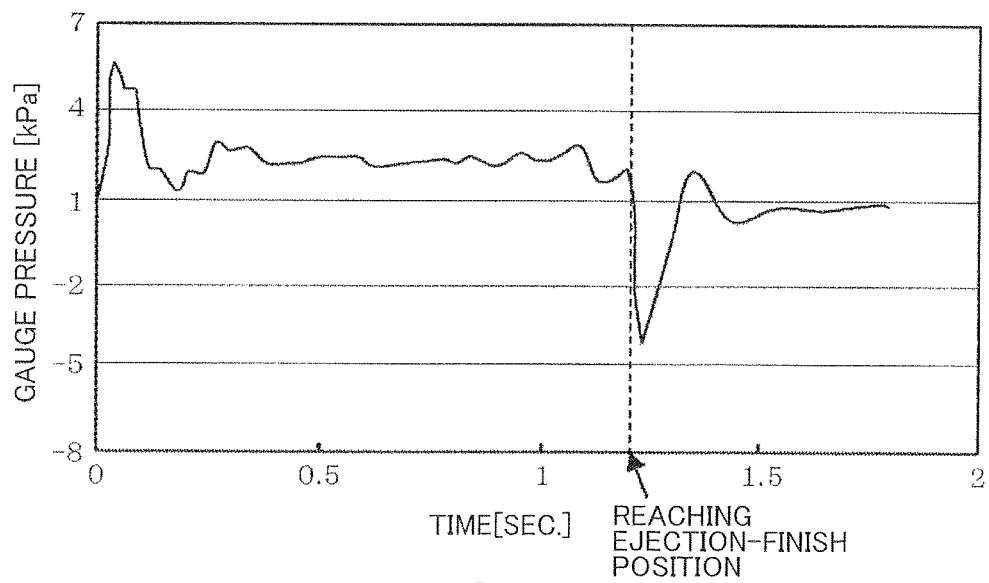
FIG. 19 is a graph showing the change of the feed pressure of the tube pump with time in Example 1.
Figure 20:
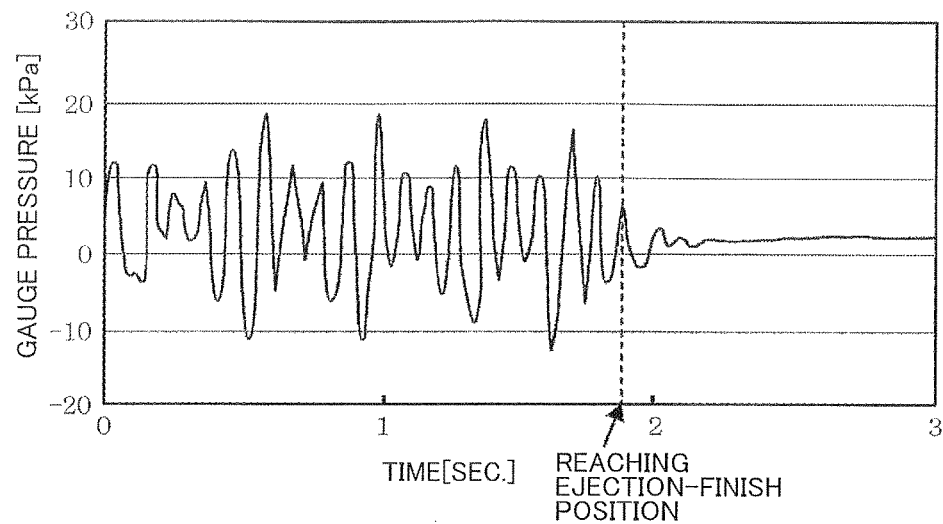
FIG. 20 is a graph showing the change of the feed pressure of the tube pump with time in Comparative Example 1.
Figure 21:
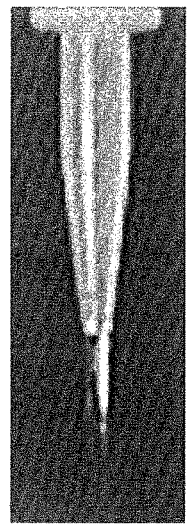
FIG. 21 is a copy of a photograph showing the ejecting state of the resist liquid from a nozzle in Example 1.
Figure 22A:
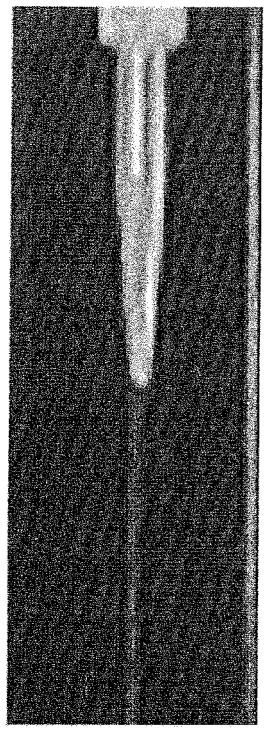
FIGS. 22A and 22B are copies of photographs showing the ejecting state of the resist liquid from a nozzle in Comparative Example 1.
Figure 22B:
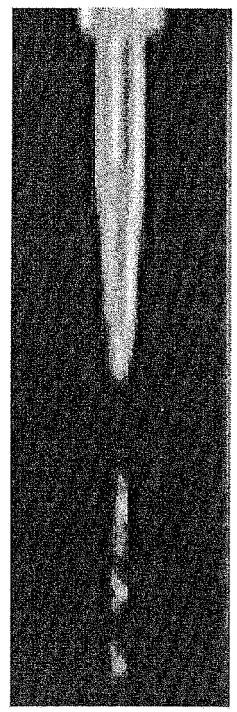

FIG. 19 shows the change of the feed pressure of the resist liquid with time in (Example 1), and FIG. 21 shows the ejecting state of the resist liquid from the nozzle 51 in (Example 1). In addition, FIG. 20 shows the change of the feed pressure of the resist liquid with time in (Comparative Example 1), and FIGS. 22(a) and 22(b) show the ejecting state of the resist liquid from the nozzle in (Comparative Example 1). In FIGS. 19 and 21, the horizontal axis represents "time", and the vertical axis represents the indication value of the manometer 56 expressed as "gauge pressure".

The experiment result of (Example 1) in FIG. 19 shows that, when the resist liquid was supplied by using only one rotor 65, the resist liquid was supplied at a stable pressure of about 2 kPa during the movement of the rotor 65. The pressure was relatively significantly changed only at the timing immediately after the movement of the rotor 65 was started and at the timing immediately after the movement of the rotor 65 was stopped. As a result, as shown in FIG. 21, the resist liquid could be ejected from the nozzle 51 without any discontinuity or interruption.

On the other hand, as shown in FIG. 20, the experiment result of Comparative Example 1 in shows that the pressure of the resist liquid at the outlet of the tube pump 6d largely pulsated at all times within a range between about +20 kPa and about −10 kPa. Due to the pulsation, there were time periods during which resist liquid was continuously ejected from the nozzle 51 as shown in FIG. 22(a); and time periods the resist liquid was intermittently ejected from the nozzle 51 as shown in FIG. 22(b). Namely, the resist liquid could not be supplied stably.

The pipe of the discharge line 501 was formed of a transparent pipe and the resist liquid flowing through the discharge line 501 toward the nozzle 51 was observed. In Comparative Example 1, it was confirmed that a lot of fine bubbles were included in the resist liquid, which could not be observed in Example 1. The reason is considered that a section of the tube 62 between the pinched parts of the tube 62 pinched by adjacent two rotors 65 were in a negative pressure, whereby the gas dissolved in the resist liquid is released to form bubbles. The supplying of a resist liquid containing bubbles will result in non-uniform coating and/or defects of a film.

(Experiment 2)

By using the same tube pump 6 as that used for Example 1, the change of the amount of the resist liquid ejected from the nozzle 51 was observed while changing the ejection-start position but maintaining the distance between the ejection-start position and the ejection-finish position.

A. Experiment Condition

Example 2-1

Figure 23:
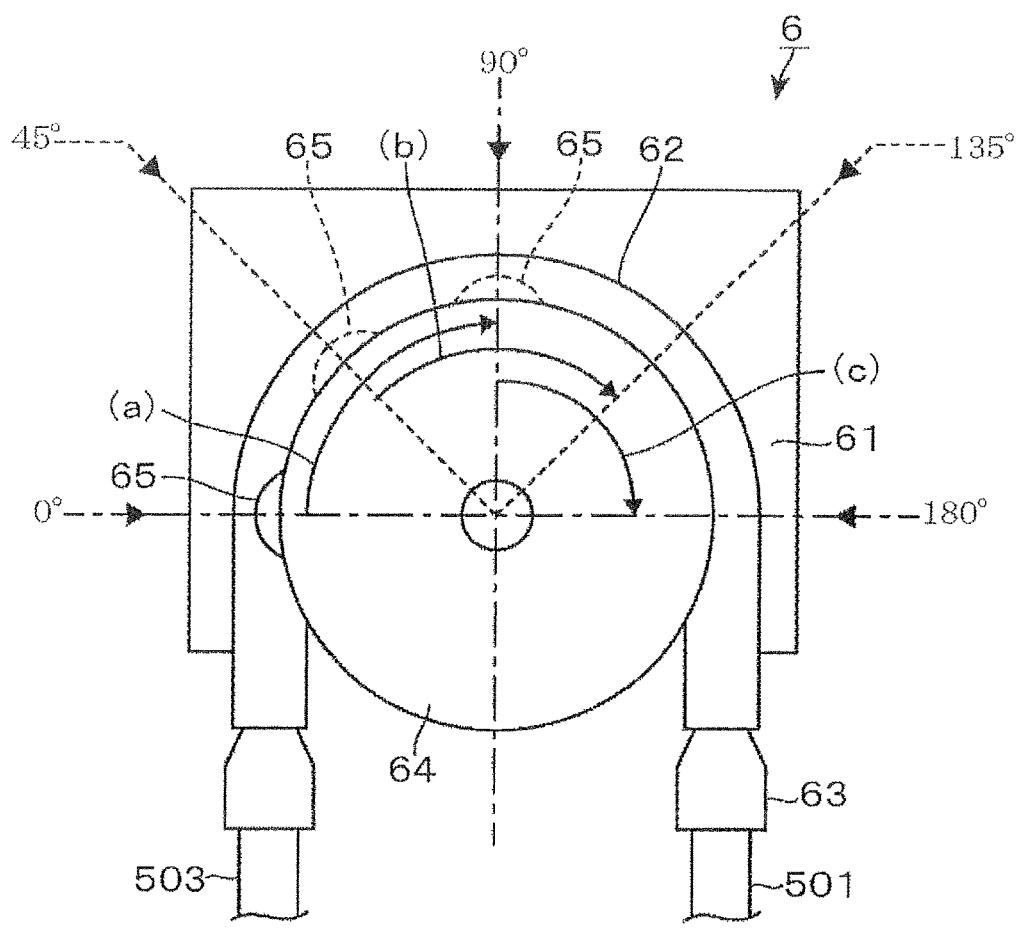
FIG. 23 is transversely-sectioned plan view of a tube pump for explaining ejection-start positions in Example 2.

As shown by the arrow with the reference character (a) in FIG. 23, the tube pump 6 fed the resist liquid to the nozzle by moving the rotor 65 from an angular position of 0 deg. as the ejection-start position to an angular position of 90 deg. as the ejection-finish position. The amount of the resist liquid ejected from the nozzle 51 was measured ten times.

Example 2-2

As shown by the arrow with the reference character (b) in FIG. 23, the tube pump 6 fed the resist liquid to the nozzle by moving the rotor 65 from an angular position of 45 deg. as the ejection-start position to an angular position of 135 deg. as the ejection-finish position. The same measurement was made as Example 2-1.

Example 2-3

As shown by the arrow with the reference character (c) in FIG. 23, the tube pump 6 fed the resist liquid to the nozzle by moving the rotor 65 from an angular position of 90 deg. as the ejection-start position to an angular position of 180 deg. as the ejection-finish position. The same measurement was made as Example 2-1.

B. Experiment Result

Figure 24:
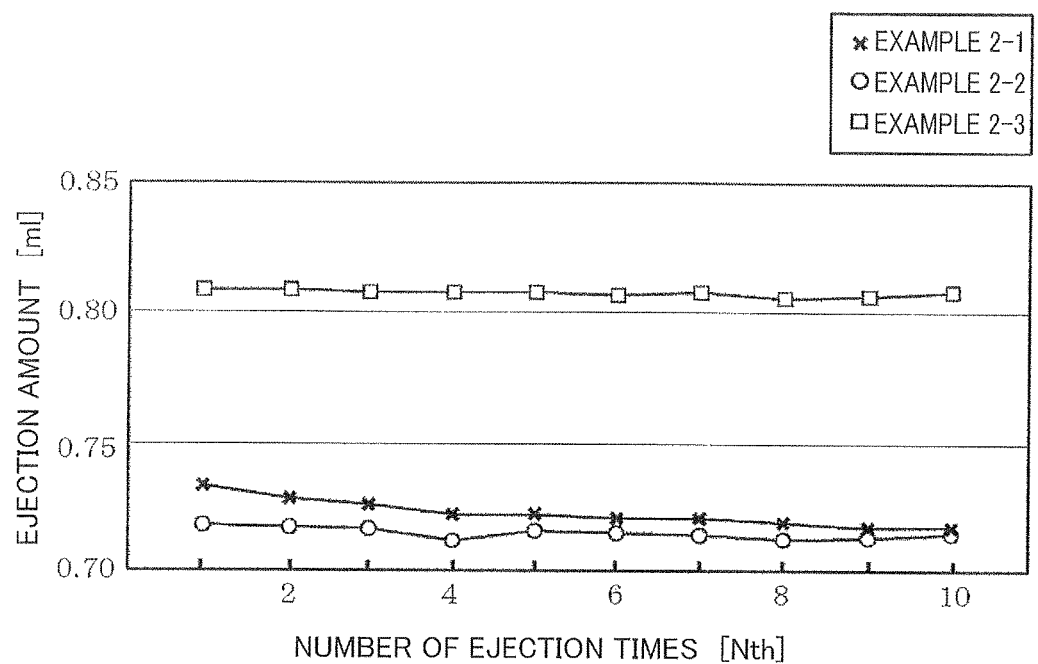
FIG. 24 is a graph showing the change of the ejection amount depending on the ejection-start position.

FIG. 24 shows experiment results of Example 2-1 to Example 2-3. The horizontal axis of FIG. 24 represents the number of times at which the resist liquid was ejected from the nozzle 51, and the vertical axis represents the measures amount of the ejected resist liquid each time. In FIG. 24, the result of (Example 2-1) is shown by plots of crosses (X), the result of (Example 2-2) is shown by plots of white circles (○), and the result of (Example 2-3) is shown by plots of white squares (□).

The experiment results in FIG. 24 show that, in any of Example 2-1 to Example 2-3, in the case where the ejection-start position of the rotor 65 was unchanged, the amount of the ejected resist liquid was substantially constant, regardless of the number of supply times of the resist liquid. On the other hand, the average ejection amount of the resist liquid was 0.722 ml in Example 2-1; the average ejection amount in Example 2-1 was 0.716 ml which is slightly smaller than Example 2-1; and the average ejection amount in Example 2-3 was 0.807 ml, which is considerably larger than Example 2-1 and Example 2-2.

The exact reason that the amount of resist liquid ejected from the nozzle 51 varies depending on the ejection-start position of the rotor 65 is not clear, but it is considered that the elastic restoring force for restoring the shape of the deformed (pinched) tube 62 differs depending on the position of the tube 62 due to the arrangement profile of the tube 62.

As described above, from the experiment results of Example 2-1 to Example 2-3, it was found that the amount of the resist liquid ejected from the nozzle 51 is greatly affected by the ejection-start position of the rotor 65. Thus, in the tube pump 6 in which the processing liquid is discharged therefrom by one rotor 65, it was found that the same amount of the resist liquid can be stably supplied to each wafer W by maintaining the ejection-start position of the rotor 65 at the same position.

What is claimed is:

1. A processing liquid supplying apparatus comprising a feed pump provided in a supply passage, wherein by means of the feed pump, said processing liquid supplying apparatus ejects a processing liquid supplied from a processing liquid source to a process object via an ejecting part, the feed pump including:
   a resilient tube serving as a part of the supply passage;
   a guide member extending along an axial direction of the tube to support an outer surface of the tube;
   a squeezing member that moves along the axial direction of the tube with the tube being pinched between the squeezing member and the guide member, thereby to feed the processing liquid;
   a moving mechanism that moves the squeezing member from a first axial position of the tube at which the squeezing member starts pinching of the tube, to a second axial position of the tube at which the squeezing member leaves the tube after feeding the processing liquid toward the ejecting part;
   a shutoff valve provided in the supply passage at a position nearer to the processing liquid source than the tube so as to selectively allow or block feeding of the processing liquid into the feed pump;
   a filter provided in the supply passage at a position nearer to the ejecting part than the tube; and
   a control unit configured to output a control signal for controlling the moving mechanism and the shutoff valve such that: the squeezing member pinches the tube with a part of the supply passage between the shutoff valve and the tube being filled with the processing liquid; then the squeezing member pinching the tube moves toward a downstream side of the tube with the shutoff valve being closed, thereby to depressurize the part of the supply passage between the shutoff valve and the tube and to degas the processing liquid existing in the part of the supply passage between the shutoff valve and the tube being filled with the processing liquid, using resilience of the resilient tube that causes the resilient tube to return to its original shape; then the shutoff valve is opened to allow the degassed processing liquid flow into the tube; and then the squeezing member again pinches the tube and moves toward a downstream side of the tube to feed the processing liquid into the filter so as to filter the degassed processing liquid;
   wherein the squeezing member and the moving mechanism are configured such that only one pinched part pinched between the squeezing member and the guide member is formed between the first axial position and the second axial position of the tube, and said only one pinched part moves along the axial direction of the tube during discharging of a dose of the processing liquid toward the ejecting part.

2. The processing liquid supplying apparatus according to claim 1, wherein the squeezing member starts to move from a predetermined ejection-start axial position of the tube with the tube being pinched between the squeezing member and the guide member, when the feed pump starts feeding the processing liquid toward the ejecting part.

3. The processing liquid supplying apparatus according to claim 1, further comprising:
   a branch passage branched from the supply passage at a junction between the feed pump and the ejecting part;
   a flow passage switching unit that switches a destination of the processing liquid fed from the feed pump between the ejecting part and the branch passage; and
   a control unit configured to output a control single for controlling the flow passage switching unit such that the processing liquid fed from the pump is supplied to the branch passage when the squeezing member moves from the first axial position to an ejection-start axial position with the tube being pinched between the squeezing member and the guide member, and the processing liquid fed from the pump is supplied to the ejecting part when the squeezing member moves from the ejection-start axial position toward the second axial position.

4. The processing liquid supplying apparatus according to claim 3, wherein the branch passage merges into the supply passage at a junction located nearer to the processing liquid source than the tube, whereby the processing liquid fed from the feed pump returns to the feed pump via the branch passage when the flow passage switching unit switches the destination of the processing liquid to the branch passage.

5. The processing liquid supplying apparatus according to claim 4, further comprising a filter provided in a flow path extending from an outlet of the feed pump through the branch passage to an inlet of the feed pump.

6. The processing liquid supplying apparatus according to claim 1, wherein the feed pump is configured such that the guide member is replaceable, so that an amount of the processing liquid fed by a single feeding action of the squeezing member can be changed by using one guide member selected from a plurality of guide members having different lengths measured in the axial direction of the tube.

7. The processing liquid supplying apparatus according to claim 1, wherein the feed pump is configured such that the tube is replaceable, so that an amount of the processing liquid fed by a single feeding action of the squeezing member can be changed by using one tube selected from a plurality of tubes having different inner diameters.

8. The processing liquid supplying apparatus according to claim 1, wherein the moving mechanism carries a plurality of squeezing members, and the moving mechanism is configured such that when one of the squeezing members pinching the tube moves to feed the processing liquid, the other squeezing member or members do not pinch the tube.

9. A processing liquid supplying method that feeds a processing liquid supplied from a processing liquid source by means of a feed pump provided in a supply passage to eject the processing liquid from an ejecting part to a process object, said method comprising:

providing a feed pump having: a resilient tube providing a part of the supply passage; a guide member extending along an axial direction of the tube to support an outer surface of the tube; and a squeezing member that moves along the axial direction of the tube with the tube being pinched between the squeezing member and the guide member, thereby to feed the processing liquid;

moving the squeezing member to a first axial position of the tube to allow the tube to be pinched between the squeezing member and the guide member;

then, moving the squeezing member in the axial direction of the tube toward its downstream side with the tube being pinched between the squeezing member and the guide member, thereby feeding the processing liquid toward the ejecting part; and thereafter, separating the squeezing member from the tube;

wherein only one pinched part, which is pinched between the squeezing member and the guide member is formed in the tube between the first axial direction and the second axial direction, and said only one pinched part moves along the axial direction of the tube during discharging of a dose of the processing liquid toward the ejecting part, said method further comprising:

providing a shutoff valve in the supply passage at a position nearer to the processing liquid source than the tube so as to selectively allow or block feeding of the processing liquid into the tube, and further providing a filter in the supply passage at a position nearer to the ejecting part than the tube;

pinching the tube by the squeezing member with a part of the supply passage between the shutoff valve and the tube being filled with the processing liquid;

then moving the squeezing member toward a downstream side of the tube with the shutoff valve being closed, thereby depressurizing the part of the supply passage between the shutoff valve and the tube and degassing the processing liquid existing in the part of the supply passage between the shutoff valve and the tube being filled with the processing liquid, using resilience of the resilient tube that causes the resilient tube to return to its original shape;

then opening the shutoff valve, thereby to allow the degassed processing liquid to flow into the tube; and then pinching the tube by the squeezing member and moving the squeezing member toward a downstream side of the tube, thereby feeding the processing liquid into the filter so as to filter the degassed processing liquid.

10. The processing liquid supplying method according to claim 9, wherein the squeezing member starts to move from a predetermined ejection-start axial position of the tube with the tube being pinched between the squeezing member and the guide member, when the processing liquid is fed toward the ejecting part.

11. The processing liquid supplying method according to claim 9, further comprising:

providing a branch passage branched from the supply passage at a junction between the feed pump and the ejecting part; and a flow passage switching unit that switches a destination of the processing liquid fed from the feed pump between the ejecting part and the branch passage; and setting the flow passage switching unit so that the destination of the processing liquid is the branch passage to allow the processing liquid to be fed toward the branch passage, when the squeezing member is moving from the first axial positon to an ejection-start axial position of the tube; and setting the flow passage switching unit so that the destination of the processing liquid is the ejecting part to allow the processing liquid to be fed toward the ejecting part, when the squeezing member reaches the ejection-start axial position of the tube.

12. The processing liquid supplying method according to claim 11, wherein the branch passage merges into the supply passage at a junction located nearer to the processing liquid source than the tube, whereby the processing liquid fed from the feed pump returns to the feed pump via the branch passage when the flow passage switching unit switches the destination of the processing liquid to the branch passage.

13. The processing liquid supplying method according to claim 12, further comprising filtering by means of a filter the processing liquid which is fed from the feed pump and returned to the feed pump via the branch passage.

14. A non-transitory storage medium configured to store a computer program operating on a computer, wherein the computer program includes steps for controlling a processing liquid supplying apparatus configured to eject a processing liquid to a processing object from an ejecting part, the computer is configured to execute the computer program to control the processing liquid supplying apparatus to perform the processing liquid supplying method according to claim 9.

* * * * *